United States Patent [19]

Klopfer et al.

[11] 4,128,731

[45] Dec. 5, 1978

[54] PREPARATION OF 1,1,1-TRICHLORO-2,2-BIS(4-HYDROXYPHENYL)ETHANE

[75] Inventors: Howard J. Klopfer; John R. Campbell, both of Clifton Park, N.Y.

[73] Assignee: General Electric Company, Schenectady, N.Y.

[21] Appl. No.: 803,650

[22] Filed: Jun. 6, 1977

[51] Int. Cl.$^2$ ............................................. C07C 39/24
[52] U.S. Cl. ................................................. 568/726
[58] Field of Search .................... 260/619 A; 568/726

[56] References Cited

U.S. PATENT DOCUMENTS

| | | | |
|---|---|---|---|
| 1,977,627 | 10/1934 | Greenhalgh | 260/619 A |
| 2,435,014 | 1/1948 | Niederl | 260/619 A |
| 3,207,794 | 9/1965 | Haines et al. | 260/619 A |

*Primary Examiner*—Joseph E. Evans
*Attorney, Agent, or Firm*—Joseph T. Cohen; Charles T. Watts

[57] ABSTRACT

The compound 1,1,1-trichloro-2,2-bis(4-hydroxyphenyl)ethane can be prepared by effecting reaction between phenol and chloral in a solvent medium comprising aqueous sulfuric acid of a concentration of from 75 to 88%.

3 Claims, No Drawings

PREPARATION OF 1,1,1-TRICHLORO-2,2-BIS(4-HYDROXYPHENYL)ETHANE

This invention relates to a process for making a certain trichloro diphenyl ethane. More particularly, the invention is concerned with a process for making 1,1,1-trichloro-2,2-bis(4-hydroxyphenyl) ethane having the formula

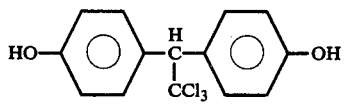

which comprises reacting under condensation conditions phenol with chloral in a solvent medium comprising aqueous sulfuric acid of a concentration of from 75 to 88%, thus eliminating the need for acetic acid used in prior art reactions of the same type.

Diphenyl trichloro-ethanes, such as 1,1,1-trichloro-2,2-bis(4-hydroxyphenyl) ethane (hereinafter identified as "p,p-isomer"), have in the past been prepared by the condensation of phenol and chloral in a solvent medium comprising sulfuric acid and acetic acid. [See E. Ter-Meer, Ber., 7, 1201 (1874); E. Von Auwers, Ber., 36, 1878 (1889).] While the crude product obtained by this method is in an acceptable yield, it is often highly colored and contaminated with substantial quantities of by-products, notably 1,1,1-trichloro-2-(4-hydroxyphenyl)-2-(2-hydroxyphenyl) ethane (hereinafter identified as "o,p-isomer"). In addition to the above disadvantages, the acetic acid as a cosolvent adds to the cost of the process. Moreover, because of the high heat of solution between the concentrated sulfuric acid and the acetic acid, it is necessary to introduce highly sophisticated cooling means, which again adds to the cost of the process.

One of the more sought-after attributes of a process is to be able to carry out the process on a continuous basis. This usually means that at some stage in the process, the reaction product should be capable of being readily removed and the process is capable of recycling either unused portions of the initial reactants or else to refurbish depleted reactants to bring them up to a level where they can be used again on a continuous basis in making more of the desired reaction product. The use of acetic acid as a cosolvent makes it difficult to carry out a recycle step in making the compund of formula I.

We have now unexpectedly discovered thaty by either diluting concentrated sulfuric acid with water or using $H_2SO_4$ of a lower concentration one can effect reaction between phenol and chloral without the necessity of using acetic acid as a cosolvent with its attendant disadvantages. We have also found that the water-diluted sulfuric acid exerts a moderating influence on the temperature at which the reaction is carried out so that only slightly elevated temperatures are required for the purpose, and cooling means normally employed when acetic acid is employed as the cosolvent, are required only under minimal circumstances. By using the diluted sulfuric acid without the acetic acid, the color is often better at any stage of the process.

We have also discovered that, contrary to the problems associated with the use of acetic acid in a recycle process, our process, because of its ability to substitute water for acetic acid (hereinafter referred to as "diluted $H_2SO_4$ acid system"), is especially amenable to a continuous process, to ready removal of the reaction product, and to recycling of unused reactants by raising the quality of the depleted $H_2SO_4$ to a level which is required for again successfully conducting the reaction. This is accomplished by recycling the reaction mother liquors of the diluted $H_2SO_4$ acid system employed in the practice of our invention. The advantages derived from using the diluted $H_2SO_4$ acid system are greatly improved over the use of an $H_2SO_4$-acetic acid system. When an $H_2SO_4$-acetic acid system is subjected to a recycle action, the color generated in the reaction product becomes intensified so that highly colored, often deep purple, products are obtained. In contrast to this, the recycling of the diluted $H_2SO_4$ mother liquors produces products uniformly of a lower color.

In addition, the diluted $H_2SO_4$ mother liquor is also more easily recycled in the course of our process than that derived from the $H_2SO_4$-acetic acid system because dilution of the $H_2SO_4$-acetic acid mother liquor by water formed in the reaction process results in unacceptably long reaction times. In contrast to this, the diluted $H_2SO_4$ acid system retains good reaction times as long as care is taken to maintain the concentration of the $H_2SO_4$ within the narrow limits more specifically discussed below. Moreover, reconstitution of the acid mother liquor to permit the $H_2SO_4$ to regain its original acid strength in our diluted $H_2SO_4$ acid process by using, for instance, sulfur trioxide, is more easily achieved with our process than when working with the $H_2SO_4$-acetic acid system, because the acetic acid interferes with returning the $H_2SO_4$ to the required concentration or strength.

The sulfuric acid employed is aqueous sulfuric acid of a concentration of from 75 to 88% $H_2SO_4$. As pointed out above, extreme care must be used in choosing the correct concentration of sulfuric acid in the reaction medium. The use of too concentrated a sulfuric acid solution leads to poor yields of the desired compound of formula I because of sulfonation of the reaction product; while the use of too dilute a sulfuric acid materially reduces the reactivity of the reaction system, resulting in poor yields of product. If the condensation of the chloral and phenol is carried out only in concentrated sulfuric acid, for instance in sulfuric acid of 96% concentration, it will be found that the desired p,p-isomer will maximize at a percent yield of about 45 to 50% and thereafter will decline markedly to a yield of below 10% after a period of about 3 hours.

We have found that when concentrated sulfuric acid is diluted down to the desired concentration, considering all the water which is present in the concentrated aqueous sulfuric acid solution and in the added water, if the ratio of the weight of the $H_2SO_4$ to the weight of $H_2O$ in the total system is within the range of 4:1 to 10:1, maximum yields in the range of 80 to 85% of the desired p,p-isomer can be obtained. Additionally, the yield of the less desirable o,p-isomer is minimized. We have found that when the ratio of the weight of the $H_2SO_4$ to the weight of added $H_2O$ is less than 3:1 or more than 10:1, either oils are obtained which are difficult and often almost impossible to process to obtain the desired p,p-isomer, or else the yield of the desired p,p-isomer drops markedly.

The ratio of the diluted sulfuric acid to the other ingredients can be varied widely and is not critical. Generally, on a weight basis, we can employ from about 0.75 to 10 or more parts of the diluted sulfuric acid per part phenol.

The temperature at which the reaction is carried out between the phenol and chloral is advantageously maintained below 50° C. and usually within the range of between 15° to 35° C. In some instances this may require modest cooling means in order to maintain adequate control of the reaction which is normally somewhat exothermic. The critical concentration range of the $H_2SO_4$ will vary slightly with the temperature of reaction.

Generally, in carrying out the reaction, it is convenient to charge concentrated sulfuric acid (90-98% $H_2SO_4$) and an amount of water needed to reduce the concentration of the $H_2SO_4$ to the desired level, to a reaction vessel equipped with stirrer, thermometer, and means for introducing nitrogen. Alternatively, it may be more advantageous to use the less expensive commercially available sulfuric acid grades, e.g., 66° (93%) and 60° (77.7%), and mix the two together to obtain the most desirable concentration, i.e., 75-88%, specified previously, since this avoids the high heat of dilution and the requirement for expensive cooling means when diluting down concentrated $H_2SO_4$.

An inert atmosphere is advantageously employed throughout the reaction. This may be accomplished by applying a nitrogen blanket or other inert gas above the surface of the reaction mixture.

Thereafter, the phenol is added and subsequently followed by the chloral, which itself is advantageously added in small amounts over a period of time of about 0.1 to 2 hours or more. Generally, at least 2 mols of the phenol should be added per mol of the chloral, and advantageously we have found that we can employ from 2 to 6 or more mols of the phenol per mol of the chlora. After stirring the reaction mixture for a period of time ranging from 1 to 24 hours or more, the precipitate which forms can be either filtered directly or the reaction mixture can be poured into a large volume of water, the precipitate is filtered and washed with additional water and a lower halogenated hydrocarbon, e.g., $CHCl_3$, methylene chloride, etc. The powder thus obtained consists primarily of the p,p-isomer and is advantageously vacuum-dried at temperatures ranging from 60° to 100° C. to yield the desired product.

In order that those skilled in the art may better understand how the present invention may be practiced, the following examples are given by way of illustration and not by way of limitation. All parts are by weight unless otherwise indicated. Since the reaction is exothermic, cooling was resorted to in order to maintain the designated temperatures.

Analyses of the reaction products in some of the following examples to determine the presence of the desired materials and other ingredients, was carried out by silylating samples of the isolated reaction product with bis(trimethylsilyl) acetamide in the manner described by Klebe et al in J.A.C.S. 88, 3390 (1966). This involved adding a previously silylated weighed sample of bisphenol-A to serve as an internal standard. The silylated mixture was then analyzed by vapor phase chromatography using a 6 feet × ⅛ inch Se-30 column with a temperature program of 150° to 300° C. at 10° C. per minute. VPC (vapor phase chromatographic) retention times for the o,p-isomer having the formula

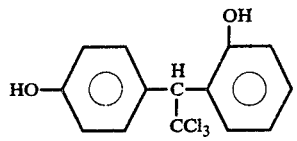

and the p,p-isomer of formula I (which is the more desirable isomer for making polycarbonate resins by phosgenation) are 12.0 and 13.0 minutes, respectively. All reactions were carried out under a nitrogen blanket.

EXAMPLE 1

This example was carried out using a mixture of sulfuric acid of 96% concentration and acetic acid (as generally taught in the prior art) as the medium for reaction between the phenol and the chloral. More particularly, a reaction vessel equipped with stirrer, thermometer, nitrogen inlet and addition funnel was charged with 178.8 grams of 96% aqueous sulfuric acid, and 105 grams acetic acid. This solution was cooled to 25° C. and 177 grams (1.88 mols) phenol was added, again with cooling to 20° C., to form a solution of the ingredients. The addition funnel was then charged with 99.8 grams (0.677 mol) chloral which was added dropwise over a 12 minute period while the temperature was maintained below 30° C. with an ice bath. Stirring was continued for about 18 hours, after which time the reaction mixture was poured into 400 ml water and the filtered precipitate was washed with several 400 ml portions of water and methylene chloride. The water-washed precipitate was found to be difficult to slurry, filter, or dry in that it tended to clump together. Vacuum drying at a temperature of about 70° C. gave 207.4 grams of a product still slightly wet with water and which had a color ranging from pink to light purple. This product comprised mainly the compound of formula I and contained about 8.1%, by weight, of the o,p-isomer. Slurrying the product with methylene chloride and then removing the methylene chloride, gave 187.6 grams (about 86.2% yield of the p,p-isomer of formula I) of a very light pink powder containing 2.1% of the o,p-isomer. The powder thus obtained after the methylene chloride treatment was easier to slurry, filter, and dry.

EXAMPLE 2

In this example, acetic acid was omitted and instead water was used in its place while employing the same procedure and other reactants as described in Example 1. More particularly, 268.2 grams 96% $H_2SO_4$ and 50 grams of water (50 ml) were mixed together in the reaction vessel, thus diluting the $H_2SO_4$ from about 96% to 81.0% by weight. The same amount of phenol and chloral were added in the manner described in Example 1 and further precipitation and washing the precipitate with water and vacuum drying yielded the desired p,p-isomer, slightly off-white in color, in an amount equal to 208.4 grams, which represents a yield of about 97.0%. Trituration with methylene chloride, similarly as in Example 1, followed by vacuum drying, gave 184.3 grams of the desired p,p-isomer in the form of a white powder (yield of 84.7% based on chloral), which had 1.9% of the o,p-isomer of formula II.

EXAMPLE 3

This example illustrates the effect of using sulfuric acid alone without the addition of any water. More particularly, employing the same procedure and reactants of Example 1 except that acetic acid was omitted and 357.6 grams of 96% $H_2SO_4$ were used instead of the 178.8 grams of 96% $H_2SO_4$ of Example 1. After adding the phenol and chloral and carrying out the reaction similarly as in Example 1, it was found that a solid did not precipitate from the reaction mixture; pouring the resultant oil into water after the 18 hours of stirring at room temperature (25°–30° C.) still did not give any solid product. Examination of the reaction product showed a rapid formation of the p,p-isomer to a maximum yield of about 48% after about ¾ of an hour, and subsequent decomposition of the product to sulfonated products wherein after 2¾ hours, there was only 6.4% of the p,p-isomer.

EXAMPLE 4

In this example, a series of tests were conducted whereby the 96% $H_2SO_4$ was diluted with different amounts of water and the reaction carried out similarly as in Example 2. This example is intended to show the criticality of using the right amount of water with the concentrated sulfuric acid in order to obtain not only good yields of the p,p-isomer and small amounts of the o,p-isomer but also to obtain solid products rather than oils which are difficult and often impossible to process to obtain the desired product. Otherwise, the conditions of reaction and the proportions of ingredients were essentially the same as those recited in Example 2. The following Table I shows the results of these tests using varying amounts of water with the sulfuric acid.

TABLE I

| Test No. | a % $H_2SO_4$ | Ratio of Wt. $H_2SO_4$ Wt. $H_2O$ | Percent Yield Based on Chloral | |
|---|---|---|---|---|
| | | | o,p-isomer | p,p-isomer |
| 4A | 61.6 | 1.79:1 | | oil[b] |
| 4B | 71.8 | 3:1 | | oil[b] |
| 4C | 76.7 | 4:1 | 5.0 | 82.2 |
| 4D | 81.0 | 5.36:1 | 4.0 | 84.7 |
| 4E | 85.4 | 8:1 | 3.4 | 85.9 |
| 4F | 89.6 | 19:1 | — | 41.0 |
| 4G | 96 | 24:1 | | oil[b] |

[a]After dilution with water.
[b]No solid product obtained.

It will of course be understood by those skilled in the art that other conditions of reactions and ratios of reactants and ingredients can be employed, many examples of which have been given above, without departing from the scope of the invention. For instance, the ratio of the mixture of sulfuric acid and the water to the weight of the phenol and chloral can be varied widely depending on the critical weight ratio between the sulfuric acid and the water. Persons skilled in the art will have no difficulty in ascertaining the optimum conditions taking into account the effects of varying the ratio of the sulfuric acid to the water based on the above-described examples.

The composition of matter obtained in accordance with the practice of the present invention has many uses. Thus, the dihydroxy diphenyl trichloro-ethane of formula I can be used as a precursor intermediate for making the monomer composition having the formula

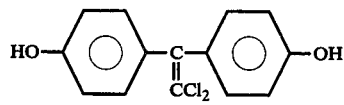

This latter dichloro-ethylene compound can be treated with a phosgenating agent such as phosgene, diphenyl carbonate, etc., to make polycarbonate resins which are useful in the preparation of flame-retardant and fire-resistant molded products such as housings for calculators, grills and dashboards for automobiles, etc.

What we claim as new and desire to secure by Letters Patent of the United States is:

1. The process for making a trichloro-ethane of the formula

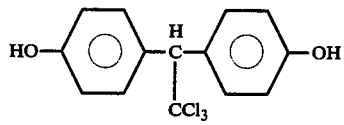

which comprises reacting at a temperature of from 15° to below 50° C. under condensation conditions phenol and chloral in a solvent medium consisting essentially of aqueous sulfuric acid of 76.7 to 85.4% concentration.

2. The process as in claim 1 wherein the ratio of the weight of the aqueous $H_2SO_4$ to the weight of the phenol ranges from 0.75 to 10.

3. The process as in claim 1 wherein the reaction product is washed with water and methylene chloride.

* * * * *